United States Patent [19]

Andersen

[11] Patent Number: 4,519,402
[45] Date of Patent: May 28, 1985

[54] SYRINGE FOR COLLECTING A LIQUID SAMPLE

[75] Inventor: Jørgen Andersen, Herlev, Denmark

[73] Assignee: Radiometer A/S, Copenhagen, Denmark

[21] Appl. No.: 526,899

[22] Filed: Aug. 26, 1983

[30] Foreign Application Priority Data

Aug. 27, 1982 [DK] Denmark .................... 3855/82

[51] Int. Cl.³ ............................................. A61B 5/14
[52] U.S. Cl. .................................... 128/765; 128/766
[58] Field of Search ............... 128/763, 764, 765, 766; 604/236, 237, 245, 246, 247, 248

[56] References Cited

U.S. PATENT DOCUMENTS

| 3,943,917 | 3/1976 | Johansen ................ 128/763 |
| 3,960,139 | 6/1976 | Bailey . |
| 3,978,846 | 9/1976 | Bailey . |
| 4,065,360 | 12/1977 | Kreb ................ 128/765 X |
| 4,133,304 | 1/1979 | Bailey . |
| 4,206,768 | 6/1980 | Bailey . |
| 4,257,426 | 3/1981 | Bailey ................ 128/765 X |
| 4,266,558 | 5/1981 | Akhavi . |
| 4,266,559 | 5/1981 | Akhavi . |
| 4,299,238 | 11/1981 | Baidwan et al. . |
| 4,327,745 | 5/1982 | Ford ................ 128/765 |
| 4,340,067 | 7/1982 | Rattenborg ........... 128/763 |
| 4,340,068 | 7/1982 | Kaufman ........... 604/125 X |
| 4,373,535 | 2/1983 | Martell . |
| 4,448,206 | 5/1984 | Martell ............... 128/765 |

FOREIGN PATENT DOCUMENTS

| 0047806 | 3/1982 | European Pat. Off. . |
| 0047176 | 10/1982 | European Pat. Off. . |
| 3041563 | 5/1981 | Fed. Rep. of Germany . |
| WO81/03456 | 12/1981 | PCT Int'l Appl. . |

Primary Examiner—Edward M. Coven
Attorney, Agent, or Firm—Hubbell, Cohen, Stiefel & Gross

[57] ABSTRACT

A syringe for collecting a sample of blood or another liquid comprises a syringe cylinder and a piston arranged displaceably therein. One or more axially extending recesses are formed in the inner wall of the syringe cylinder axially spaced from the inner end thereof. The recess or recesses contain a material which is pervious to gas and impervious to liquid, such as a hydrophobic material, a hydrophilic material with capillary effect, or a material which swells when contacted by liquid. The sample collecting chamber within the cylinder may be vented to the atmosphere by placing the piston in the recessed area of the cylinder. Arterial blood may then pass into the syringe under arterial blood pressure, and the flow of blood into the syringe is automatically stopped when the sample collecting chamber of the syringe has been filled, because blood cannot pass the liquid impervious material arranged in the recesses. The axial innermost portion of the inner cylinder wall, which is not recessed, may cooperate with the piston in a conventional manner so as to provide a suction effect within the blood collecting chamber, if desired.

8 Claims, 5 Drawing Figures

U.S. Patent  May 28, 1985  4,519,402
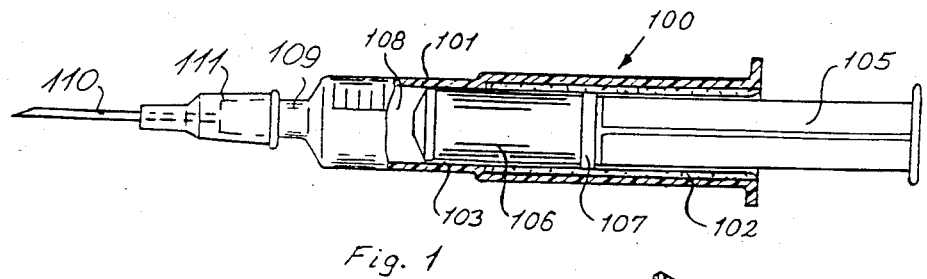
Fig. 1
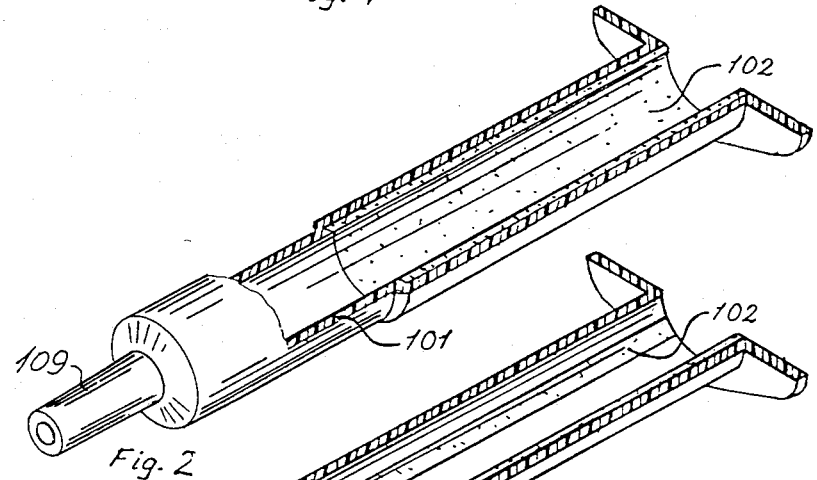
Fig. 2
Fig. 3
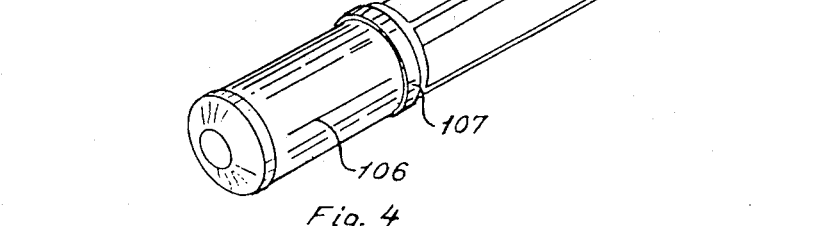
Fig. 4
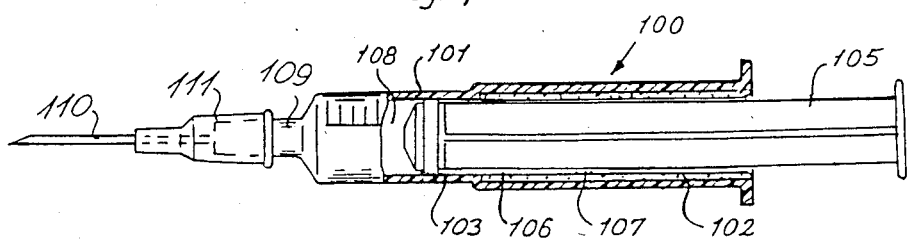
Fig. 5

SYRINGE FOR COLLECTING A LIQUID SAMPLE

BACKGROUND OF THE INVENTION

1. Field of the Invention

The present invention relates to a syringe for collecting a liquid sample. While the syringe according to the invention may be used for collecting samples from liquids of any type, it is especially suited for collecting a blood sample, such as an arterial blood sample, from a blood vessel for subsequent blood gas analysis.

The blood parameters determined by blood gas analysis, such as the partial pressure of oxygen ($pO_2$), the partial pressure of carbon dioxide ($pCO_2$), and the acidity (pH), may be influenced and changed when the blood sample comes into contact with the ambient atmosphere, and, consequently, it is necessary to take special measures in order to avoid or reduce such contact.

2. Description of the Prior Art

Such blood collection syringes, wherein the blood collecting chamber is vented to the atmosphere through a venting passage while a blood sample is collected, and wherein the venting passage may be closed when a suitable amount of blood has been collected in the syringe, are well known, for example from U.S. Pat. Nos. 3,943,917, 4,133,304, 4,206,768 and 4,257,426 and German Offenlegungsschrift No. 3,041,563. However, all of these known blood collecting syringes require certain manual operations subsequent to the collection of a blood sample in order to close the venting passage.

U.S. Pat. Nos. 3,960,139, 3,978,846, 4,266,558, 4,266,559, 4,327,745, 4,340,067, and 4,373,535, PCT publication No. WO 81/03426, and published European patent applications Nos. 47,176 and 47,806 all disclose blood samplers comprising a collecting chamber, which is vented to the atmosphere through a filter or closure element, which is pervious to gas, but impervious to liquid or becomes impervious to liquid when wetted thereby. This latter structure causes the flow of blood sample into the blood collecting chamber of the syringe to be automatically stopped, when the chamber has been filled so that blood comes into contact with the filter or closure element.

In most of these prior art syringes the venting passage opens into the blood collecting chamber of the syringe at such a position or such positions that a complete discharge of air or gas from the blood collecting chamber is dependent on the position in which the syringe is held when a blood sample is collected. The prior art also comprises a syringe disclosed in U.S. Pat. No. 4,299,238.

However, the above mentioned U.S. Pat. No. 4,340,067 discloses a syringe comprising a piston, which is provided with a peripheral sleeve of a hydrophilic material, such as porous filter paper. This porous sleeve forms part of a venting passage and allows air or gas to escape from the sample collecting chamber in any rotational position of the syringe provided that the piston rod is upwardly directed. When blood comes into contact with the hydrophilic sleeve surrounding the piston, the hydrophilic material swells and closes the venting passage defined between the cylinder wall and the outer peripheral wall of the piston. In order to reduce the risk that blood passes the piston, so that the user of a syringe may come into contact with such blood, the hydrophilic piston sleeve used in the known syringe could advantageously have been replaced by a sleeve made from a hydrophobic material.

However, despite the kind of porous material from which the piston sleeve is made, this prior art syringe has the disadvantage that it cannot be used for creating subatmospheric pressure within the blood collecting chamber, for example when the blood pressure in an artery from which a blood sample is to be collected, is insufficient for causing blood to flow through the hollow needle of the syringe into the blood collecting chamber.

SUMMARY OF THE INVENTION

The present invention provides an improved syringe of the above type, and the syringe according to the invention comprises a syringe cylinder having a sample inlet passage at one end, and a piston displaceably arranged within the cylinder and sealingly engaging with the inner surface of the cylinder so as to define a sample collecting chamber therein, part of the inner surface, which is axially spaced from said one end of the syringe cylinder being defined by a material which is pervious to gas and impervious to liquid, so as to define at least one venting passage for the sample collecting chamber in at least one axial position of the piston.

In the syringe according to the invention the piston may be of the conventional type which is in sealing engagement with the inner peripheral wall of the syringe cylinder. This means that when the displaceable piston is moved from the said one end of the syringe cylinder, in which the sample inlet passage is defined, to the adjacent end of the cylinder surface part defined by the gas pervious material, a suction effect may be created so that a blood sample may be sucked from an artery or a blood vessel in case the blood pressure is insufficient to cause the blood to flow through the hollow needle into the syringe cylinder. When the blood pressure is sufficient to cause such flow, the piston may be moved to a position where the peripheral surface of the piston is in engagement with the gas pervious material, whereby a venting passage for the sample collecting chamber is provided.

The gas pervious material may be arranged between peripherally spaced, axially extending ridges formed on the inner surface of the syringe cylinder, so that the piston is radially compressed when moved into engagement with these ridges in order to define the venting passage between the piston and the inner cylinder wall. In the preferred embodiment, however, the material is arranged in at least one recess defined in the inner surface of the cylinder. Such recesses may extend in a substantially axial direction and be uniformly peripherally spaced. Each recess may be rectilinear, tortuous, helical, or have any other suitable shape. The thickness of the gas pervious material arranged in the recess or recesses may be substantially equal to or exceed the radial depth of the recess or recesses.

The said gas pervious material is preferably a hydrophobic filter material, whereby the risk that blood passes the piston and comes into contact with the user of the syringe is substantially reduced. The gas impervious material may also be a solid hydrophobic material having a rough or granular surface exposed to the inner space of the syringe cylinder. Other suitable gas pervious materials are materials which swell when contacted by liquid, such as cellulose fibres, viscose rayon, wool, cotton, and jute. Also substances, which swell and form a gel when they come into contact with aqueous liquids, may be used. Examples of such substances are starch-based polymer materials of the type used in babies' napkins and in bandages, or freeze-dried compressed products. Other gas pervious materials which may be used are hydrophilic materials with capillary effect, such as thread-like or yarn-like materials of cellulose, viscose rayon, wool, and cotton.

In the preferred embodiment the recess in which the gas pervious material is arranged is annular and extends along the total periphery of the inner cylinder surface. During collection of a sample the syringe is normally held in a position in which the piston rod is upwardly directed. Therefore, when the gas pervious material is arranged in an annular recess, gas or air may always escape from the sample collecting chamber at the uppermost part of that chamber.

BRIEF DESCRIPTION OF THE DRAWING

The invention will now be further described with reference to the drawings, wherein FIG. 1 is a side view and partially sectional view of a syringe in accordance with the invention, FIGS. 2 and 3 are perspective and partially sectional views of alternative embodiments of the cylinder of the syringe shown in FIG. 1, FIG. 4 is a perspective view of a piston or plunger for use in connection with the syringe cylinders shown in FIGS. 2 and 3, and FIG. 5 is a side view and partially sectional view of a syringe as that shown in FIG. 1 with another type of piston or plunger.

The syringe 100 shown in FIG. 1 comprises a syringe cylinder 101, which is made from a suitable material such similar to glass or plastic, and which may be provided with a gas impervious barrier layer. The syringe 100 also comprises a pison or plunger 106 having a piston rod 105 and a sealing ring 107. The syringe cylinder 101 is provided with a hollow neck 109, which has a frustoconical outer peripheral surface. A hollow needle 110 is mounted on a socket 111, which has an inner frustoconical surface which is complementary to that of the neck 109, so that the socket 111 may be mounted on the neck 109. All of these elements are well known in connection with syringes for use in collecting samples for blood gas analysis. The piston 106 and the inner end of the syringe cylinder 101 define a blood collecting chamber 108 which is in communication with the bore of the hollow neck 109 and the hollow needle 110.

As best shown in FIGS. 2 and 3, one or more axially extending recesses 102 are formed in the inner wall of the cylinder 101. The recesses 102 extend from the open end of the syringe cylinder 101 to a position axially spaced from the cylinder end, which is provided with the hollow neck 109. In FIG. 2 the recess extends annularly along the total periphery of the syringe cylinder so as to form a cylinder section of an enlarged inner diameter. In the embodiment shown in FIG. 3, a number of axially extending, narrow recesses are uniformly peripherally spaced.

The recess or recesses 102 receive a gas pervious and liquid impervious material, such as a hydrophobic filter material, for example micro-porous polyethylene or polypropylene, or micro-porous polytetrafluoro-ethylene, for example of the type marketed under the trade name TEFLON.

When a blood sample is to be collected from an artery, the piston 106 is positioned in such an axial position that the volume of the blood collecting chamber 108 substantially corresponds to the desired volume of the blood sample, and in that position the piston sealing ring 107 must be in engagement with the gas pervious material arranged in the recesses 102. The pointed free end of the hollow needle 110 is now inserted into an artery so that arterial blood may flow through the needle 110 and into the chamber 108 under the arterial blood pressure. Gas or air may then escape from the blood collecting chamber 108 through a venting passage formed by a space 103 defined between the peripheral outer wall of the piston 106 and the inner wall of the syringe cylinder 101 and by the gas pervious material arranged within the recess or recesses 102. When all of the air has been expelled from the chamber 108 and blood has penetrated into the space 103 up to the sealing ring 107, further progress of the blood is stopped, because gas, but not blood, can pass through the hydrophobic material in the recesses, and the hollow needle may now be removed from the artery.

As the hydrophobic material contains air or gas some contact between such gas and the blood within the chamber 108 will exist. In order to reduce contamination of the collected blood sample by gas the piston 106 in FIGS. 1 and 4 has a relatively long axial length, and the sealing ring 107 is positioned at the outer end of the piston. This means that the blood within the chamber 108 is in contact with the gas containing hydrophobic material only through the relatively long, narrow space 103.

If necessary, these gas contamination problems may be further reduced by using a hydrophilic or swelling material in the recesses 102. The relatively long piston 106 shown in FIGS. 1 and 4 may be replaced by a short conventional piston as that shown in FIG. 5. In that case subatmospheric pressure or suction may be provided by moving the piston from its innermost position adjacent to the neck 109 to a position adjacent to the inner end of the recesses 102. This may be of importance in cases where the arterial pressure is not sufficient to cause blood to flow into the vented blood collecting chamber 108.

It should be understood that various changes and modifications of the embodiment shown above may be made within the scope of the present invention. Thus the recesses 102 may be shaped in any desired manner, and other kinds of pistons may be used in connection with the syringe.

I claim:

1. A syringe for collecting a liquid sample comprising a syringe cylinder having an end wall defining a sample inlet passage, and a piston having a peripheral contact surface sealingly engaged with the inner surface of the cylinder, the piston being displaceable between a sampling position in which the piston is axially spaced from the cylinder end wall so as to define a sample collecting chamber within the cylinder, and a position closer to said cylinder end wall, the inner cylinder surface including a surface part which comprises a material pervious to gas and impervious to liquid and which extends axially across the contact surface of the piston when the piston is in its sampling position, so as to define at least one venting passage for the sample collecting chamber at at least one axial position of the piston.

2. A syringe according to claim 1, wherein said material is arranged in at least one recess defined in the inner surface of the cylinder.

3. A syringe according to claim 2, wherein said material is selected from the group consisting of hydrophobic filter materials, materials which swell when contacted by liquid, and hydrophilic materials with capillary effect.

4. A syringe according to claim 3, wherein said material is selected from the group consisting of micro-porous polyethylene, polypropylene, and polytetrafluoroethylene.

5. A syringe according to claim 2, wherein said recess is annular and extends along the total periphery of the inner cylinder surface.

6. A syringe according to claim 2, wherein said material is arranged in a plurality of peripherally spaced, axially extending recesses.

7. A syringe according to claim 1, wherein the volume of the space defined in the cylinder between said one end of the cylinder and the adjacent end of the said liquid impervious material is substantially equal to the desired volume of the liquid sample to be collected.

8. A syringe according to claim 1, wherein said liquid sample is arterial blood.

* * * * *